(12) United States Patent
Schabbach et al.

(10) Patent No.: US 7,569,187 B2
(45) Date of Patent: Aug. 4, 2009

(54) DEVICE FOR REMOVING CONSUMABLE ANALYTIC PRODUCTS FROM A STORAGE CONTAINER

(75) Inventors: Michael Schabbach, Hirschberg (DE); Karl Miltner, Frankenthal (DE); Thomas Klemm, Mannheim (DE); Rolf Baumann, Vill.-Schwenningen (DE); Meinrad Dilger, St. Georgen (DE)

(73) Assignee: Roche Diagnostics GmbH, Mannheim (DE)

( * ) Notice: Subject to any disclaimer, the term of this patent is extended or adjusted under 35 U.S.C. 154(b) by 245 days.

(21) Appl. No.: 10/263,267

(22) Filed: Oct. 1, 2002

(65) Prior Publication Data
US 2003/0039584 A1 Feb. 27, 2003

Related U.S. Application Data

(62) Division of application No. 09/489,502, filed on Jan. 21, 2000, now Pat. No. 6,475,436.

(30) Foreign Application Priority Data
Jan. 23, 1999 (DE) ................. 199 02 601

(51) Int. Cl.
*G01N 35/10* (2006.01)
(52) U.S. Cl. .............. 422/64; 422/58; 422/61; 422/93; 422/102; 436/46; 436/48; 436/164; 221/30; 221/79
(58) Field of Classification Search ............... 422/64, 422/99, 100, 58, 61, 93, 102; 436/46, 48, 436/164; 221/30, 79
See application file for complete search history.

(56) References Cited

U.S. PATENT DOCUMENTS

| | | | |
|---|---|---|---|
| 4,569,828 A * | 2/1986 | Nishizawa | 117/201 |
| 4,676,952 A | 6/1987 | Edelmann et al. | 422/72 |
| 4,872,591 A | 10/1989 | Konopka | 221/3 |
| 5,271,896 A | 12/1993 | Jakubowicz et al. | 422/63 |
| 5,332,549 A | 7/1994 | MacIndoe, Jr. | 422/63 |
| 5,464,118 A | 11/1995 | Grau et al. | 221/5 |
| 5,489,414 A | 2/1996 | Schreiber et al. | 422/64 |
| 5,510,266 A | 4/1996 | Bonner et al. | 436/43 |
| 5,554,166 A | 9/1996 | Lange et al. | 606/182 |

(Continued)

FOREIGN PATENT DOCUMENTS

DE 197 53 847 A 1 6/1999

(Continued)

OTHER PUBLICATIONS

N.M Schmidt et al.: "Understanding automation systems", 1984, Texas Instruments, USA XP002238432.

*Primary Examiner*—Jill Warden
*Assistant Examiner*—Jyoti Nagpaul
(74) *Attorney, Agent, or Firm*—Justin L. Sage; Roche Diagnostics Operations, Inc.

(57) ABSTRACT

A method and a device for removing an analytic consumable product, in particular a test element, from a storage container having chambers which are sealed by foils from which the consumable product is pushed out by means of a plunger (7) can be optimized in that the magnitude of the thrusting force exercised by the plunger (7) during its forward motion can be controlled in dependence on the plunger (7) position.

24 Claims, 7 Drawing Sheets

U.S. PATENT DOCUMENTS

| | | |
|---|---|---|
| 5,630,986 A | 5/1997 | Charlton et al. ............... 422/64 |
| 5,632,410 A | 5/1997 | Moulton et al. ............... 221/79 |
| 5,720,924 A | 2/1998 | Eikmeier et al. ............ 422/102 |
| 5,777,210 A | 7/1998 | Voelker et al. ........... 673/53.05 |
| 6,136,270 A | 10/2000 | Maes et al. ................... 422/64 |
| 6,145,762 A | 11/2000 | Orloff et al. ............. 239/533.2 |

FOREIGN PATENT DOCUMENTS

| | | |
|---|---|---|
| DE | 198 54 316 A 1 | 10/1999 |
| EP | 0 138 152 A2 | 4/1985 |
| EP | 0 357 935 A1 | 3/1990 |
| EP | 0 565 970 B1 | 10/1993 |
| EP | 0 622 119 A1 | 11/1994 |
| EP | 0 630 609 A3 | 12/1994 |
| EP | 0 732 590 A3 | 9/1996 |
| EP | 0 738 666 A3 | 10/1996 |
| EP | 0 821 233 A3 | 1/1998 |
| EP | 0 821 234 A3 | 1/1998 |
| WO | WO 97/02487 | 1/1997 |

* cited by examiner

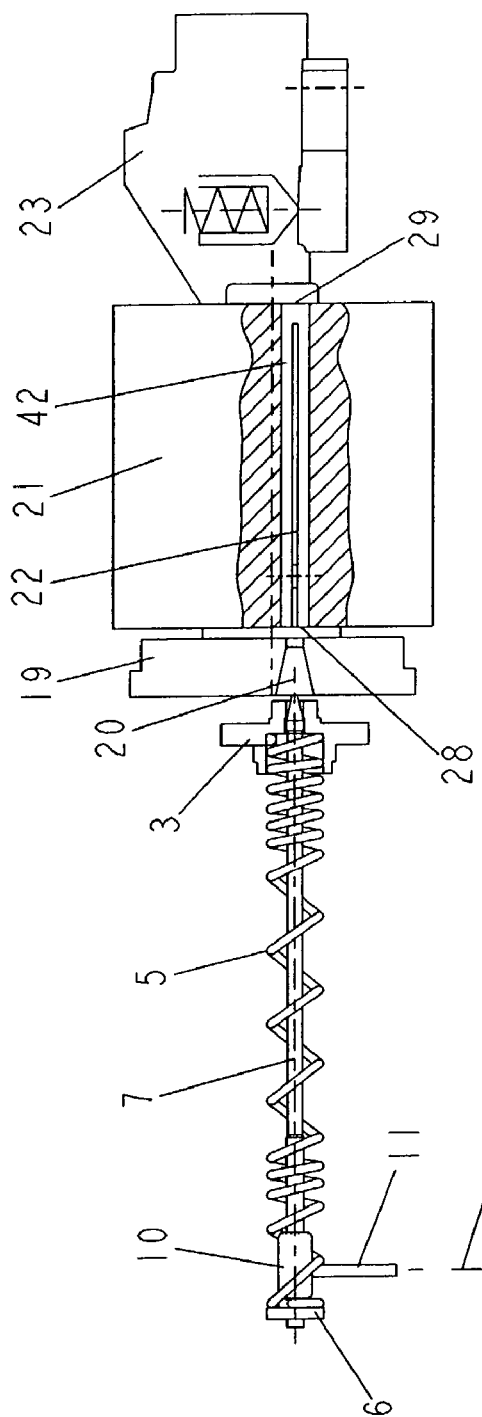
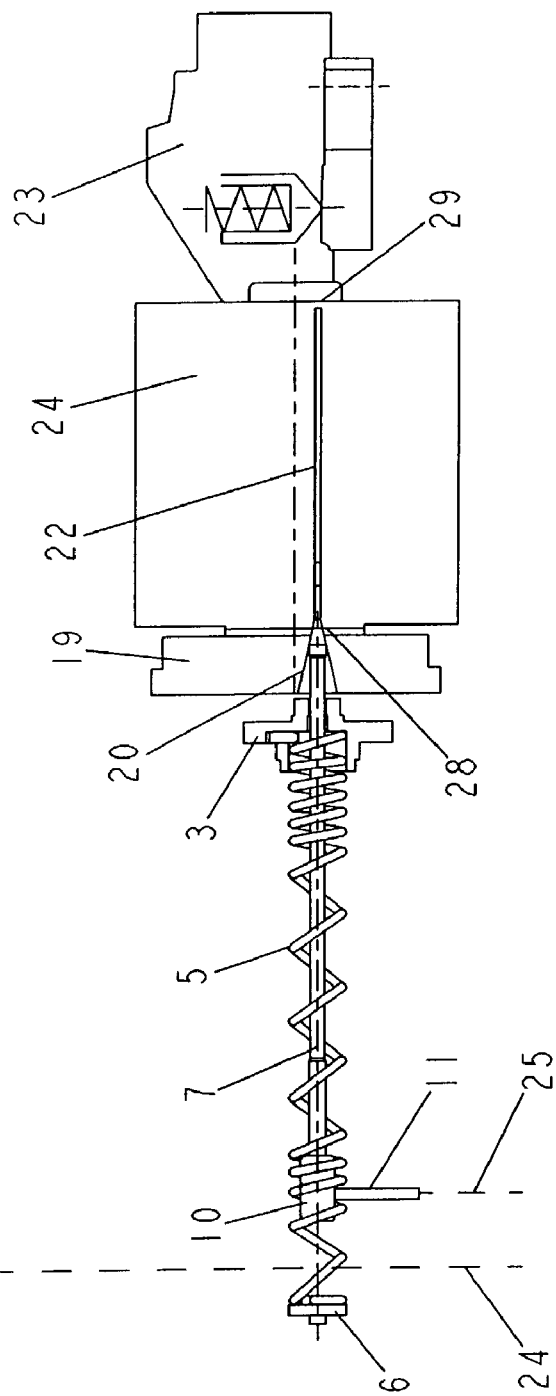
FIG. 5
FIG. 6

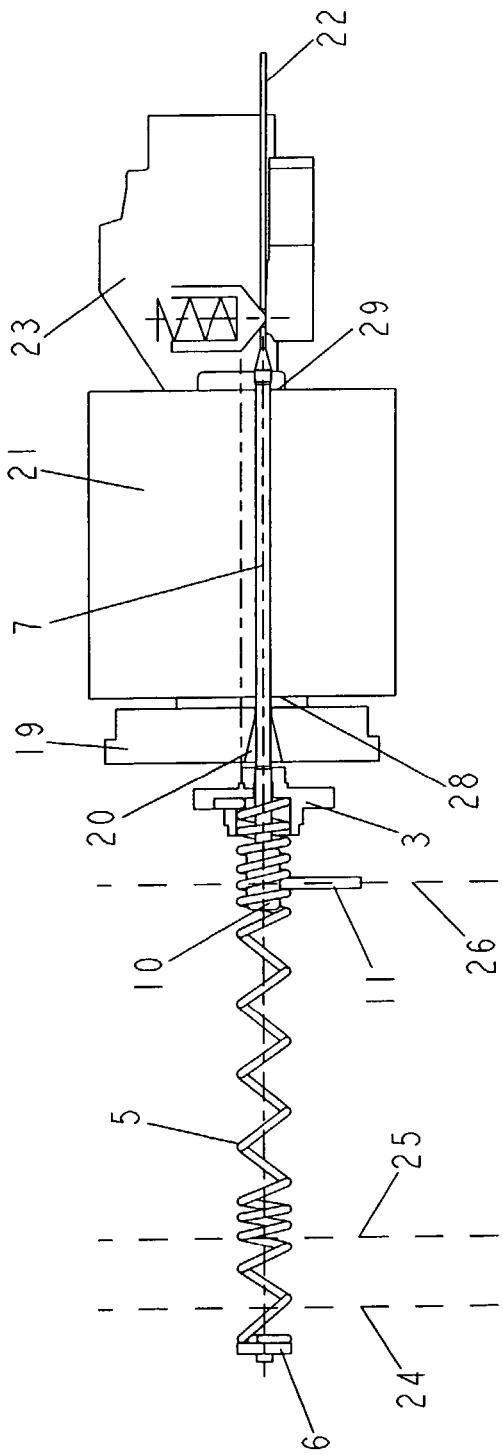
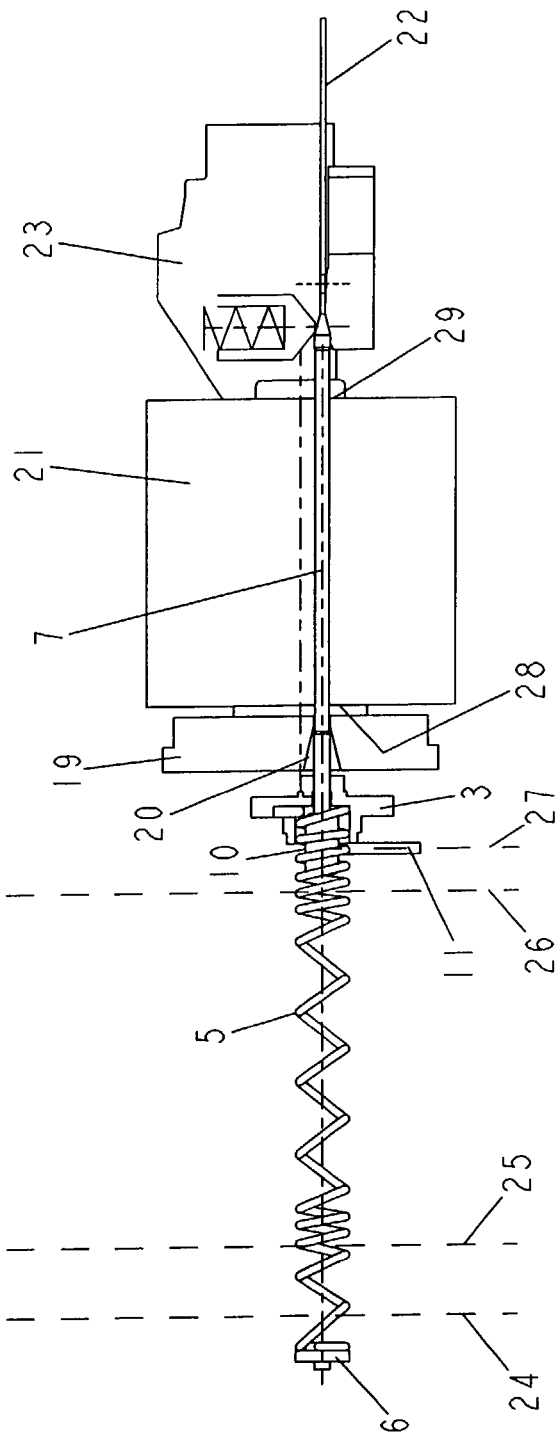
FIG. 7
FIG. 8

DEVICE FOR REMOVING CONSUMABLE ANALYTIC PRODUCTS FROM A STORAGE CONTAINER

CROSS REFERENCE TO RELATED APPLICATIONS

This application is a divisional of U.S. patent application Ser. No. 09/489,502, filed on Jan. 21, 2000 now U.S. Pat. No. 6,475,436, which claims priority to DE 199 02 601.7, filed Jan. 23, 1999.

BACKGROUND AND SUMMARY OF THE INVENTION

The invention concerns a device and a corresponding method for removing a consumable analytic product, in particular a test element, from a storage container having one or more chambers. The chambers each contain one or more consumable products and each have a removal opening for removal of a consumable product and an insertion opening lying across from the removal opening for the introduction of a plunger to transport the consumable product being removed. The removal opening and the insertion opening are each sealed with a foil (also designated as a sealing foil) for storing the consumable product. In order to remove a consumable product, a plunger is displaced by a drive unit and the consumable product is transported by the plunger out of the storage container chamber.

Carrier-bound quick tests have been established for use in laboratories specializing in the chemical and biochemical analysis of solid and liquid sample materials and, in particular, also for use outside of such specialized laboratories. Such carrier-bound quick tests are based on specially developed dry chemistry and can even be carried out by laymen in a simple and uncomplicated way despite the complex reactions frequently used and the associated sensitive reagents.

A conventional example for carrier-bound quick tests is a test element for determining the blood sugar content in diabetics. Diagnostic test elements configured in a strip-like fashion are also designated as test strips. Conventional embodiments are e.g. single or multiple field test strips for urine analysis and various indicator papers. Since other types of carrier-bound tests are also available in addition to test elements having strip shapes, one speaks, in general, of analytic test elements.

Within the context of the invention, analytic test elements can be evaluated visually or by an apparatus. Test elements which can be evaluated using an apparatus include e.g. test elements which can be evaluated optically, in particular photometrically, and electrochemical sensors and the like. Analytic test elements of this kind and other consumable products are packed in a storage container to protect them from damaging environmental influences such as light, moisture and mechanical effects or to store them under sterile conditions. In addition to test elements, consumable analytic products can include e.g. lancets or sampling elements.

Since these types of analytic consumable products have been thoroughly described in prior art and are completely familiar to one of average skill in the art in a plurality of embodiments, detailed description thereof is unnecessary here. Instead, reference is made to e.g. the following documents: DE-A 19753847.9, EP-A 0138152, EP-A 0821233, EP-A 0821234, EP-A 0630609, EP-A 0565970 and WO 97/02487.

Analytic consumable products are stored in a storage container made from a rigid material to protect them from the influence of optical radiation or from moisture in the air and from soiling, bacteria and dust as well as from mechanical influences. Should the storage container hold a plurality of consumable products, these are normally accommodated in individual chambers, wherein the chambers can each contain one or a plurality of consumable products. A storage container can also contain various types of analytic consumable products, e.g. test elements and lancets, each in their own chamber.

In order to remove a consumable product, one of the chambers is opened by rupturing the foils sealing the removal opening and the insertion opening. Consumable products can thereby be removed from chambers when needed without opening the other chambers so that the consumable products contained in the unopened chambers can continue to be stored in a secure fashion.

The storage containers and chambers can be configured in the must differing of fashions and contain, in many cases, a supply of drying agent for protection against moisture. The storage containers can be provided with a data storage medium, e.g. a label having a readable print, a barcode label or a magnetic strip upon which charge-specific data and optional additional information concerning the analytic consumable product can be stored and recalled.

The analytic consumable products can be removed from the storage container either manually or, preferentially, using a mechanical device, wherein the consumable products remaining in the storage container within the unopened chambers continue to be protected by the individual sealing foils. Removal of the consumable product is effected by pushing it out of the chamber using a plunger.

Storage containers for analytic consumable products and the corresponding apparatus for removal of the consumable products are thoroughly described in prior art and are familiar to one of average skill in the art in a plurality of embodiments. In this connection, reference is made e.g. to the following documents: EP-A 0622119, EP-A 0732590, EP-A 0738666, U.S. Pat. No. 5,489,414, U.S. Pat. No. 5,510,266, U.S. Pat. No. 5,720,924 and, in particular, U.S. Pat. No. 5,632,410 as well as DE-A 19854316.

The storage containers, also designated as magazines, are normally conceived for use in a measuring apparatus, in particular in a compact measuring apparatus. In order to accept a storage container in a measuring apparatus in which a consumable product is to be removed from the storage container with the assistance of a plunger, appropriate means can be provided, in particular, for the precise positioning of the storage container relative to the functional components of an analytic apparatus, in particular relative to a plunger, for removal of the consumable product.

Removal of the consumable product is often automated, e.g. to prevent improper operation or to increase user friendliness. In these cases, the plunger effecting removal of a consumable product is moved by a drive unit including an electrical drive motor and optionally a transmission. Examples of conventional manual, motor driven and automated devices for the removal of analytic consumable products from storage containers are described in the documents cited above.

The storage containers with which the invention is concerned are closed on each of two oppositely disposed openings with foils which must be ruptured when the consumable product is removed. The plunger initially penetrates through the foil covering the insertion opening and into the chamber of the storage vessel where it pushes against the consumable product to be removed. The foil covering the removal opening is then torn open in an outward direction by the front end of the consumable product in feeding direction and the consumable product is pushed out of the chamber or brought into a working position. An intrinsic property of this transport procedure is that relatively large forces are required in certain regions of the transport path, e.g. when penetrating through the two foils or when positioning a test element in a predetermined position of a measurement holder, whereas only relatively small thrusting forces are required during the remaining transport path.

The choice of materials and thickness of the foils which are used to seal the openings in the storage container chambers is limited by two requirements. On the one hand, they must be sufficiently strong to provide adequate protection and must not constitute a mechanical weak point during handling of the storage container. On the other hand, the foil cannot be too strong, since it must be ruptured by the plunger or by the consumable analytic product using the pressure imparted by the thrusting force of the plunger.

Particularly in small, battery operated compact analysis apparatus, one has the additional conflicting requirement that the speed with which the consumable product, in particular a test element, is to be removed must be high and, on the other hand, the battery energy consumption associated therewith should be low in order to carry out as many measurements as possible using one charge of batteries.

In accordance with prior art, these technical problems regarding the force to be produced, the speed of removal of the consumable product and the energy requirements are solved with a drive unit producing an overall constant thrusting force for the plunger effected by the force development of the drive motor and by an optional transmission, which is sufficiently high as to overcome the load peaks occurring during the transport path. Whether or not this is effected through choice of a more powerful drive motor having a corresponding higher battery energy consumption or through choice of a different transmission ratio depends on the particular application, i.e. on whether or not a rapid measurement sequence or low overall battery energy consumption is more important.

According to prior art, the drive mechanism is thereby designed to overcome a maximally occurring load and is optimized between the two extremes of minimum energy consumption and maximum transport time or maximum energy consumption and minimum transport time. However, according to prior art, an actual optimal solution can not be achieved, since the drive is over-dimensioned through long stretches of the consumable product forward path, since it is configured for the maximum occurring load and, in dependence on the design, cannot optimally satisfy both requirements with respect to speed and energy use in these regions.

Departing from this prior art, it is the underlying purpose of the invention to improve a device of the above mentioned kind for removing a consumable analytic product, in particular a test element, from a storage container as well as an associated method in such a manner that the requirements with respect to removal speed of the consumable product as well as with regard to minimizing the amount of energy consumption associated therewith are simultaneously improved, in particular, for very compact structures of an associated device.

In order to achieve this purpose, in the above mentioned device and in a respective corresponding method, the magnitude of the thrusting force exercised by the plunger during its thrusting motion for removal of a consumable product is controlled in dependence on the plunger position. The fundamental idea underlying the present invention is that the two above mentioned contradictory requirements with respect to rapid removal and low energy consumption can be simultaneously optimized using a plunger drive whose thrusting force changes in a load-adapted fashion in dependence on the thrusting path.

Within the framework of the present invention, it has been surprisingly discovered that the extremely difficult requirements in devices for removal of a consumable analytic product from a storage container can be solved using a plunger whose thrusting force changes as a function of the thrusting path. It has furthermore turned out that such a path or location dependent thrusting force can be effected in a simple fashion so that the overall removal process can be optimized simultaneously with respect to both the speed and the energy consumption requirements and not, as had previously been thought necessary, with regard to one requirement only or in the sense of a compromise solution.

For example comparative tests have shown, that a conventional drive optimized to the saving of energy requires a transport time of 20 seconds to remove a test strip from a drum-shaped magazine and, in a battery driven measuring apparatus, more than 500 test strips can be measured. If, on the other hand, the drive is optimized for rapid removal speed, the transport time assumes values of approximately 4 seconds and only 50 test strips can be measured with one battery charge. In contrast thereto, a device configured in accordance with the invention has transport time values between 4 and 5 seconds and more than 500 test strips can thereby be measured with one battery charge.

Using the invention, goals are thereby achieved which those of average skill in the art had been attempting to achieve for some time. In addition, the limitations with regard to the material and the thickness of the foil are less important with a device in accordance with the invention so that a larger number of more economical materials or materials which are better suited for the particular application are available.

In order to achieve particularly good results with respect to the removal speed of the consumable product, the associated energy consumption, as well as with regard to mechanical requirements and the associated costs, the following features are preferentially used individually or in combination with each other.

A first preferred feature can provide that the thrusting force be controlled in dependence on the thrusting path through which the plunger has traveled. The thrusting path is thereby preferentially determined relative to a component having a fixed position with respect to the device. This can e.g. be the initial position of the plunger, the end position of the plunger or the position of one of the foils. Alternatively, an absolute position measurement of the plunger is also possible.

In addition, the removal of a consumable analytic product can be advantageously improved by increasing the thrusting force during at least one of the following operational conditions: when the plunger penetrates through the foil covering the insertion opening, when the consumable product penetrates through the foil covering the removal opening, when positioning the removed consumable product into a predetermined working position, or when expelling a used consumable product out of a predetermined working position.

In this context, a working position is any predetermined, defined position which a consumable product must assume for its intended use, e.g. the location of a sample receptacle or a position in which an analytic measurement is carried out. The consumable product must normally be precisely positioned at such working positions so that corresponding guides or abutment elements are provided leading to an increase in the thrusting force needed to transport the consumable product. In general, the device in accordance with the invention can effect increased thrusting forces required in those regions in which increased load occurs, e.g. in the above mentioned positions, whereas the thrusting force can be lower in other regions along the forward path of the plunger. In particular, energy consumption is minimized, since an increased thrusting force is provided only in those regions where the plunger must overcome increased load.

In accordance with an additional preferred feature, the device is configured in such a fashion that the thrusting speed of the plunger is reduced in regions having increased thrusting force and increased in regions having reduced thrusting force. Using this rule, the overall transport time for removal of the consumable product can be particularly well optimized while taking into consideration the associated energy consumption.

A desired thrusting force-thrusting path dependence can, in principle, be realized using purely electronic means, wherein the thrusting motion of the plunger is controlled by electronic regulation of the drive unit. Towards this end, e.g. the power or the rate of revolution of the drive motor can be controlled or a transmission regulated. Further possibilities for electronic regulation comprise the use of stepping motors, electrically commutating motors, current regulation of the drive motor, pulse width modulation of the drive motor, or similar methods. Electronic regulation can advantageously effect a thrusting speed which is independent of the operational voltage. In general, however, such a regulation has the associated disadvantages of greater structural difficulty and expense and that the drive motor can normally not be kept at an optimized working point.

In accordance with a preferred feature of the invention, the drive unit includes a drive motor which can be driven with substantially constant drive power and/or with a substantially constant rate of revolution for effecting as optimal an energy use as possible by evenly loading the current source, e.g. a battery or a storage battery, and operating the drive motor at an operating point having good efficiency.

It has turned out within the context of the invention that these goals can be preferentially achieved when the thrusting motion of the plunger is controlled by a mechanical path control, particular a mechanical control having a cam or a curved path. A mechanical path control can have the added advantages of being simple and economical from a structural point of view while having low frictional losses. In addition, the transport position of the plunger along the thrusting path as well as the thrusting force or the thrusting velocity respectively can depend on the position of the plunger through working cooperation between the mechanical path control and the plunger without requiring the special distance or position sensor normally required by an electronic solution. The cooperative connection between the mechanical path control and the plunger can couple the position of the plunger and the thrusting force or the thrusting velocity respectively.

A mechanical path control can be effected in differing manners. In accordance with an additional advantageous feature, the path control can include a helically wound control element which can be driven by the drive unit for rotation about its longitudinal axis to control the feed of the plunger and which is connected to a carrier member to move the plunger in the thrusting direction during rotation of the control element. The rotation of the control element produced by the drive unit is thereby transformed into linear motion of the plunger.

A particularly simple structural solution can then be realized in accordance with an additional advantageous feature when the longitudinal axis of the control element extends in the direction of thrusting motion of the plunger. The plunger can thereby be disposed parallel and adjacent to the control element or, in accordance with a preferred feature, can penetrate axially through the control element to produce a particularly compact construction.

The pitch of the control element of the mechanical path control can be constant along the helically shaped winding. In this case, the driving torque of the drive unit is controlled to achieve a position-dependent thrusting force and the rate of revolution of the control element is varied to achieve a position-dependent thrusting speed.

In a preferred embodiment, the pitch of the control element changes along its helically shaped winding in correspondence with a desired thrusting force-position dependence for the plunger. In this case, and in accordance with an additional particularly preferred feature, the rate of revolution of the drive unit motor and/or the rate of revolution of the control element is substantially constant during advancement of the plunger.

A helically wound control element in accordance with the invention can be realized in a plurality of different ways. In a first advantageous configuration, the control element can include a cylindrical drum controller having a groove fashioned in the outer surface thereof, wherein the carrier member includes a tendon block engaging into the groove. The groove defines a thrust path having the desired characteristics. Conventional structures of this type include spindle drives for storage and retrieval units in high bay warehouses and are described in document EP-A 0357935. However, for the applications in accordance with the invention, and in particular for compact analysis apparatus, they tend to be rather large.

Therefore realization of a helically wound control element in the form of a cylindrical, helically wound transport spiral is particularly preferred, wherein the carrier member is configured as a carrier pin engaging into the windings of the transport spiral. When the transport spiral is turned, the carrier pin is transported in the axial direction of the transport spiral in dependence on the pitch of the transport spiral and the rate of revolution. The carrier pin is in working connection with the plunger so that the plunger is moved in a forward or backward direction in dependence on the direction of rotation of the transport spiral, with the thrusting force and thrusting velocity being determined by the transport spiral. In this manner, a particularly simple structure is realized for a device in accordance with the invention.

An analysis apparatus in accordance with the invention for analysis of a medical sample using a medical consumable product, in particular for carrying out an analysis using a test element, is characterized by comprising a device in accordance with the invention for removing an analytic consumable product from a storage container.

The device in accordance with the invention is particularly advantageously used in analysis apparatus which are operated independent of the power lines, e.g. using batteries or storage batteries. In such apparatus, the invention can have particular advantages for solving the problems associated with limited energy capacity of the battery or of the electrical power storage element while nevertheless transporting a maximum number of analytic consumable products. In addition, requirements with regard to limited power, optimized travel times for the plunger or the existence of a limited amount of space can be taken into consideration and satisfied and manufacturing costs can be kept low.

The following embodiments of the invention illustrate additional advantageous features and characteristics which are described and explained more closely below with reference to the representation of the drawings.

BRIEF DESCRIPTION OF THE DRAWINGS

FIG. 5 shows the device of FIG. 1 in a base position, FIG. 6 shows the device of FIG. 1 when passing through a foil, FIG. 7 shows the device of FIG. 1 moving a test element into a measurement position, FIG. 8 shows the device of FIG. 1 when ejecting the test element.

DETAILED DESCRIPTION OF THE DRAWINGS

Figure 1:
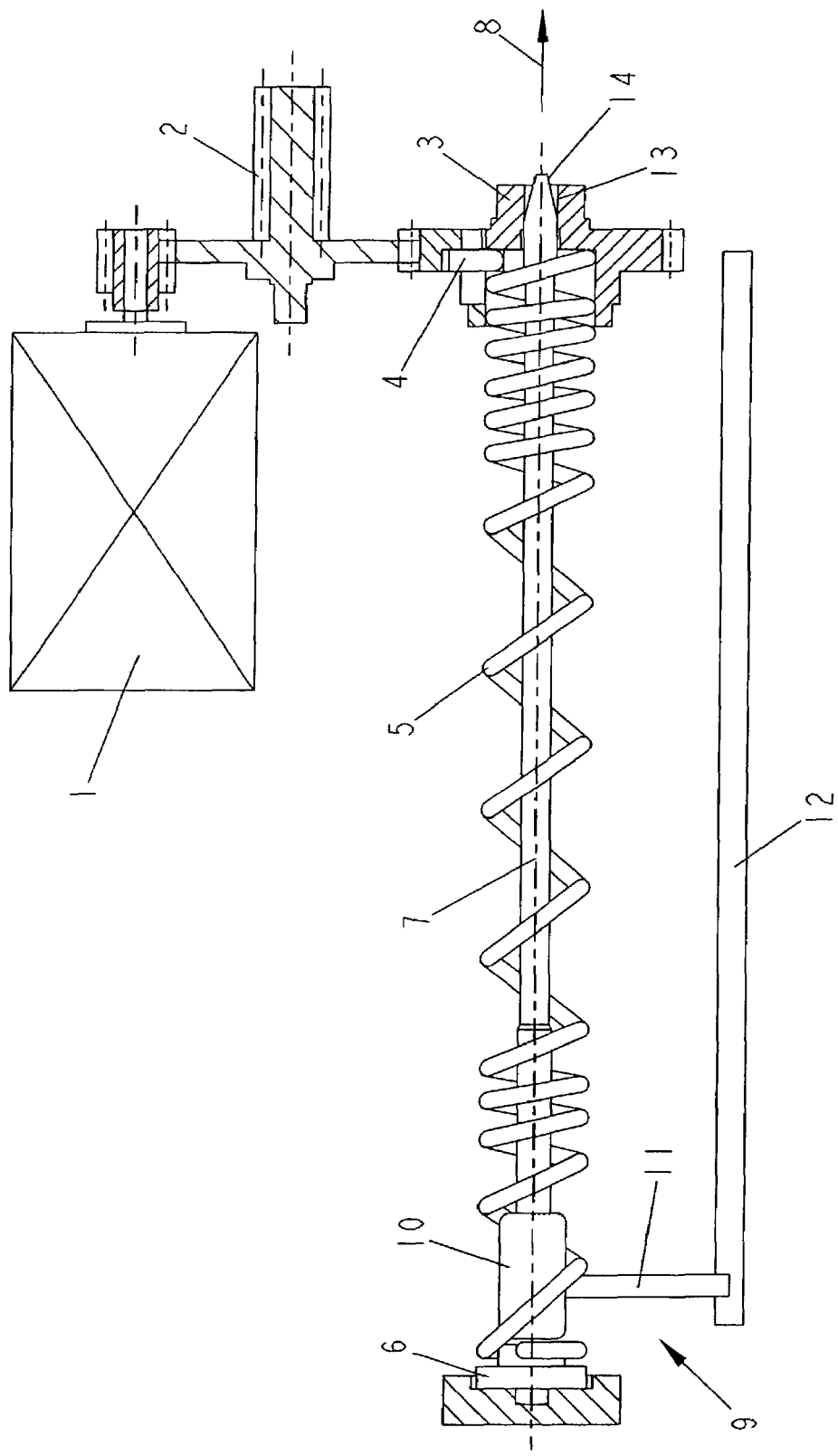
FIG. 1 shows a longitudinal section through a device in accordance with the invention.

FIG. 1 shows a preferred embodiment of a device in accordance with the invention for the removal of a consumable analytic product from a storage container (not shown in FIG. 1), which realizes the concept in accordance with the invention of a position dependent thrusting force via a mechanical path control, and is advantageous for use in very small, battery driven analytic apparatus. The device includes an electric drive motor 1, the drive force of which is transmitted by means of a transmission 2 onto a drive wheel 3. The carrier peg 4 of a cylindrical helically wound transport spiral 5 is connected to the drive wheel 3 for secure rotation therewith. The transport spiral 5 is borne for rotation at its other end in a rotation bearing 6 and can be set into rotation about its longitudinal axis by the drive.

The transport spiral 5 serves as a control element of a path control and has sections with differing pitch. It consists primarily of e.g. spring steel and can be advantageously produced from this material. However, the transport spiral 5 must not necessarily be subjected to tensile or compression loading between the drive wheel 3 and the rotation bearing 6 and must not necessarily exert an elastic spring force during operation. Although a certain elastic resiliency can be advantageous in certain cases, it is not absolutely necessary. In most applications, the transport spiral 5 can advantageously be constructed from a relatively hard, slightly elastic spring steel which is as rigid as possible, i.e. having a very high spring constant (spring rate).

A plunger 7 passes through the transport spiral 5 in an axial direction thereof. FIG. 1 shows the plunger 7 in an initial position in which it is completely pulled back into the transport spiral 5. In order to remove an analytic consumable product from a storage container, the plunger 7 is pushed out of the transport spiral 5 in the direction indicated by arrow 8. In order to thereby transform the rotational motion of the transport spiral 5 into the linear motion of the plunger 8, the plunger 7 has a carrier member 9 comprising a receptacle bushing 10 connected to the plunger 7 for secure displacement and for secure rotation therewith and also comprising a carrier pin 11 disposed on the receptacle bushing 10.

The external dimensions of the receptacle bushing 10 are sufficiently small to permit its axial displacement through the transport spiral 5. The carrier pin 11 is preferentially disposed substantially transverse to the longitudinal direction of the transport spiral 5, i.e. transverse to the thrust direction of the plunger 7. The carrier pin 11 is guided in a carrier guide 12, extending parallel to the plunger 7.

When the transport spiral 5 is set into rotation by the drive, its windings exercise a force on the carrier pin 11. This force has a component which rotates the carrier pin 11 about the plunger 7 as well as a component which moves the carrier pin 11 in the direction of the plunger 7. A rotational motion of the carrier pin 11 is blocked by the carrier guide 12 or, in special embodiments, guided thereby so that the remaining force component transports the plunger 7 through the transport spiral 5.

It is thereby advantageous when the axial dimensions of the receptacle bushing 10 are sufficiently large that it is always safely guided between the windings and cannot jam therein. The axial length of the receptacle bushing 10 should thereby advantageously be at least half of the maximum separation between two transport spiral 5 windings. It is then sufficient for the plunger 7 to be guided in the forward direction within a bushing 13; the rear end guiding is then effected by the transport spiral 5 and the receptacle bushing 10 axially displaceable therein. Other embodiments can however be advantageous in which the plunger 7 is borne at an additional location, e.g. at its rear end. The plunger 7 can, towards this end, have e.g. an axial cavity into which a guiding arbor engages at its back side.

An additional guide element can also be provided to increase the positional stability of the transport spiral 5 and/or of the plunger 7, i.e. to prevent or reduce sideward deflection or bending. Towards this end, e.g. a longitudinally slotted bushing can support the transport spiral 5 from the inside or outside. The bushing can optionally also serve the function of the carrier guide 12.

An appropriate configuration of the carrier guide 12 can simply and precisely define or control the rotational position of the plunger 7 relative to its longitudinal axis. This is e.g. particularly important when the front end of the plunger 7 comprises a blade 14, as could be advantageous to penetrate through the foil of a storage container without substantial formation of cuttings. It could then be important for the plunger 7 to have a particular orientation relative to the analytic consumable product which is to be removed from the storage container in order to guarantee secure transport. By way of example and in the event of strip-shaped test elements, the blade 14 should be approximately perpendicular to the plane of the test strip to guarantee proper transport.

The defined orientation of the plunger 7 and/or of the blade 14 relative to the consumable analytic product to be removed is effected by the carrier guide 12. This relative position can also be varied as a function of the transport path. When the carrier guide 12 is linear, the plunger 7 does not rotate during its forward motion. If, in contrast thereto, the carrier guide 12 spirals in the axial direction, the plunger 7 rotates into each position determined by the carrier guide 12.

When the direction of rotation of the transport spiral 5 is reversed, the direction of motion of the plunger 7 is likewise reversed. In dependence on the carrier member 9 embodiment and on the pitch of the transport spiral 5, it is possible for a short phase to thereby occur during which the transport spiral 5 rotates without the plunger 7 being moved. This phase ends as soon as a winding of the transport spiral 5 again seats on the carrier pin 11 to effect displacement thereof. The small amount of dead time caused thereby does not disrupt practical applications and can optionally be reduced or prevented through appropriate configuration of the coupling between the carrier pin 11 and the transport spiral 5. In addition, the carrier pin 11 can operate an end switch disposed on the front or rear end of the transport spiral 5 to terminate the transport process at the end of the transport path.

The transport spiral 5 has differing pitches along its length. It is thereby possible to vary the thrusting force exercised by the plunger 7 as well as the thrusting velocity of the plunger 7 in dependence on its displaced axial position even when the transport spiral 5 rotates with a substantially constant speed. In the sections having small pitch in which the windings of the transport spiral 5 are in close proximity to each other, the thrusting force is high and the thrusting velocity is low. In the sections in which the transport spiral 5 has a large pitch and its windings have a large separation from each other, the thrusting force is low and the thrusting velocity is high.

In consequence thereof, the drive motor 1 is loaded in a substantially more even manner during the forward motion of the plunger 7 than would be the case for a transport spiral 5 of constant pitch. This has two advantages. First of all, the apparatus battery is loaded more evenly so that more energy can be removed due to the avoidance of damaging power peaks. In addition, the drive motor 1 can be designed for an operation at an optimal operational point and as a consequence the energy efficiency is improved. This measure also reduces the overall amount of time required for displacing the plunger 7 to remove a consumable product.

As a result the varying pitch of the transport spiral 5 effects like a path dependent transmission which compensates for apparatus specific load changes acting on the plunger 7 during its forward motion, which are predetermined in dependence on the thrusting path, to load the drive motor 1 in a substantially more even fashion.

This is of course only possible within certain tolerances and one should also take into consideration the fact that the load changes occurring in individual cases and the positions at which they occur are subject to certain fluctuations. It would also be acceptable in practical applications for the rate of revolution of the drive motor 1 to decrease over time due e.g. to a decrease in remaining battery capacity or for the drive motor 1 to be subjected to small residual load changes during forward motion of the plunger 7. The magnitude of the load fluctuations or their time integral is however reduced in the configuration in accordance with the invention compared to the conventional devices so that a substantial advantage results in practical applications.

Figure 2:
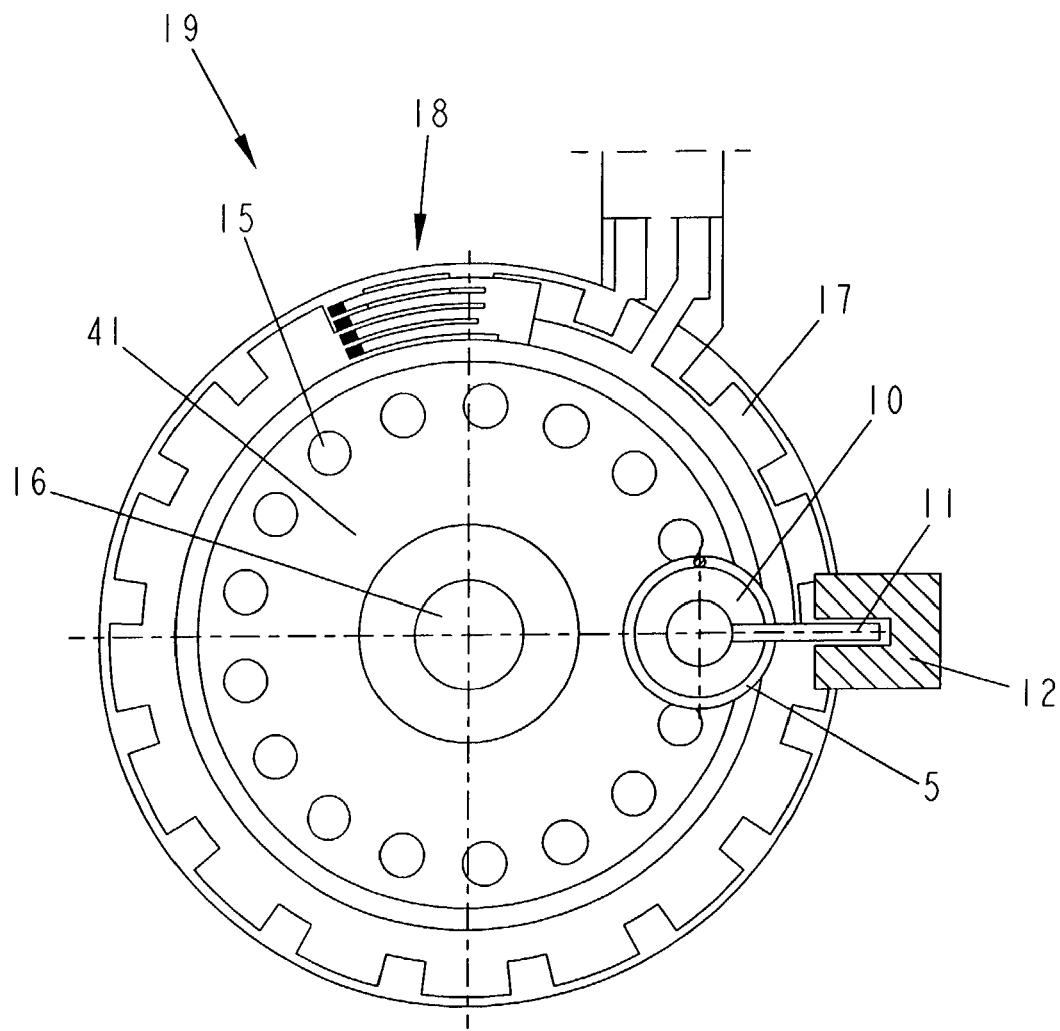
FIG. 2 shows a cross-section through the device of FIG. 1.

FIG. 2 shows a cross-section through a device in accordance with the invention illustrating the transport spiral 5, the receptacle bushing 10 and the carrier pin 11 in a linear carrier guide 12. In the example shown, the carrier guide 12 is effected by a groove in a block. Other ways of defining the position of the carrier pin 11 are easily realized by one of average skill in the art.

FIG. 2 also shows the receptacle and receiving device 19 for receiving a storage container having seventeen chambers containing consumable analytic products. The receiving device 19 thereby correspondingly includes seventeen push-through openings 15 in an apertured plate 41 which can be positioned in front of the plunger 7 and through which the plunger 7 can be guided. A guide pin 16 is disposed in the center to engage into a central bore of the storage container.

A drive (not shown) is provided for rotating the receiving device 19, wherein the positioning is effected by means of a positioning disk 17 and sliding electrical contacts 18. The storage container can have an evaluation code at its outer side which can be automatically read.

Figure 11:
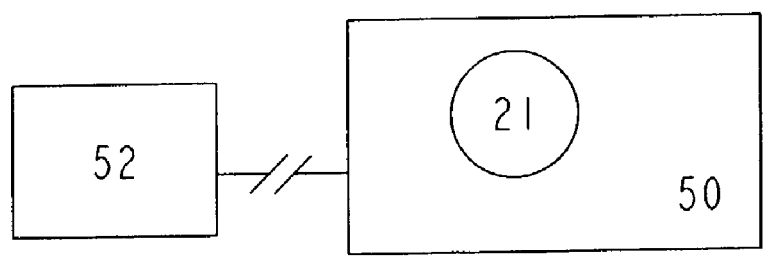
FIG. 11 shows a block diagram of an apparatus in accordance with the invention independent of power lines.

The guide pin 16 of an associated measuring apparatus engages into the central bore of the storage container and holds it in a proper position for removal of the consumable product. A toothed collar drive can e.g. be provided in the storage container at the edge of the central bore, into which a correspondingly shaped, cooperating piece can engage when the storage container is placed within an analysis apparatus 50 for rotating the storage container in the apparatus 50. See, for example FIG. 11. The storage container can be rotated within the apparatus 50 into corresponding predefined locations to facilitate, with the assistance of the plunger 7, removal of consumable products out of the storage container and preparation for measuring processes.

The push-through openings 15 are circular in shape, since the plunger 7 shaft preferentially likewise has a circular-shaped cross-section. This, however, must not necessarily be the case for the removal or insertion openings of the storage container, which are sealed by a foil. In order to keep their areas as small as possible, these openings are often non-circular in shape but have a different shape. For example, when using test strips, an elliptical or other elongated shape is advantageous, wherein the longitudinal extension lies in the direction of the test strip plane.

Figure 3:
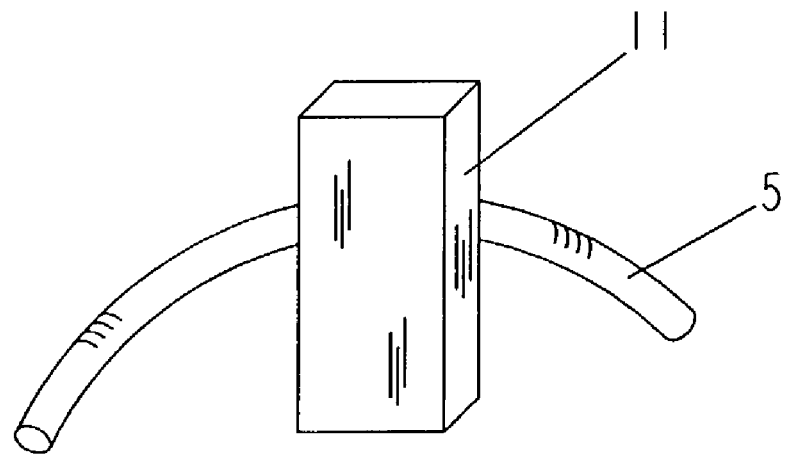
FIG. 3 shows a detail of FIG. 1.
Figure 4:
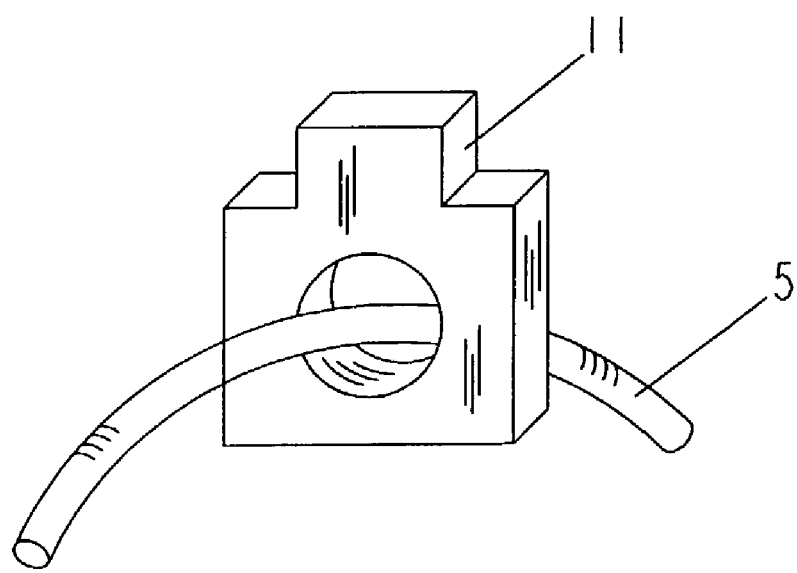
FIG. 4 shows a variation with respect to FIG. 3.

FIGS. 3 and 4 schematically show the cooperation between the carrier pin 11, guided in the carrier guide 12, and the transport spiral 5. FIG. 5 thereby corresponds to the embodiment in accordance with FIG. 1 in which the transport spiral 5 runs past the carrier pin 11 so that, when the rotational direction of the transport spiral 5 is reversed, the transport spiral 5 must be rotated to a certain extent before the plunger 7 is moved back. In the embodiment in accordance with FIG. 4, the transport spiral 5 is guided through an opening in the carrier pin 11 to reduce backlash when reversing the direction of rotation. In a different embodiment, e.g. a displaceable sleeve can also be disposed on the transport spiral 5 and is hinged for pivoting on the carrier pin 11.

FIGS. 5 to 8 illustrate various phases during operation of the device in accordance with the invention of FIG. 1. Each figure shows the transport spiral 5 with plunger 7, the receiving device 19 having a guide funnel 20 as well as a drum-shaped storage container 21 from which a test element 22 can be removed out of a chamber 42 (shown in FIG. 5 only) and displaced into a measuring device 23. The guiding funnel 20 can bring the plunger 7 into a proper position relative to the storage container 21.

In FIG. 5, the plunger 7 is located in a base position 24 at which it is pulled back into the transport spiral 5. A storage container 21 is engaged by the receiving device 19 and, using a positioning device, the chamber 42 containing the test element 22 to be removed is positioned in front of the plunger 7. The insertion opening 28 and the oppositely positioned removal opening 29 of the chamber 42 in which the test element 22 is located are sealed by a foil.

The transport spiral 5 is then set into rotation by the drive to move the plunger 7 in a forward direction and, at foil penetration 25 (shown in FIG. 6), initially push through the foil covering the insertion opening 28. Directly thereafter, the test element 22 penetrates through the foil on the removal opening 29. The plunger 7 is pushed further into the storage container 21 for additional transport of the test element 22 into the working position 26 shown in FIG. 7, wherein the test element 22 is initially transported out of the storage container 21 and subsequently positioned in a defined location within the measuring device 23. The rotational motion of the transport spiral 5 can be interrupted at working position 26 to carry out the measurement.

In FIG. 8, the test element 22 is ejected out of the measuring device 23 via an additional thrust of the plunger 7 at expulsion 27 after completion of the measurement. Subsequently, the plunger 7 is moved back into its base position in accordance with FIG. 5 by reversing the direction of rotation of the transport spiral 5 after triggering an end switch at expulsion 27. An additional end switch then stops the withdrawal motion of the plunger 7 at the base position 24.

At foil penetration 25, when positioning the test element 22 into the working position 26, and by expulsion 27 of the test element, the plunger 7 must exercise an increased thrusting force on the test element 22. In contrast thereto, only a low thrusting force is required to displace the plunger 7 out of the base position 24 towards the foil penetration position 25 as well as along the path between foil penetration 25 and positioning into the working position 26. For this reason, the pitch of the transport spiral 5 differs in differing sections so that the thrusting force exercised by the plunger 7 during its forward motion for removal of the test element 22 changes in dependence on the plunger 7 position. Even when the transport spiral 5 rotates with substantially constant speed, differing thrusting velocities result in dependence on the position of the plunger 7.

Figure 9:
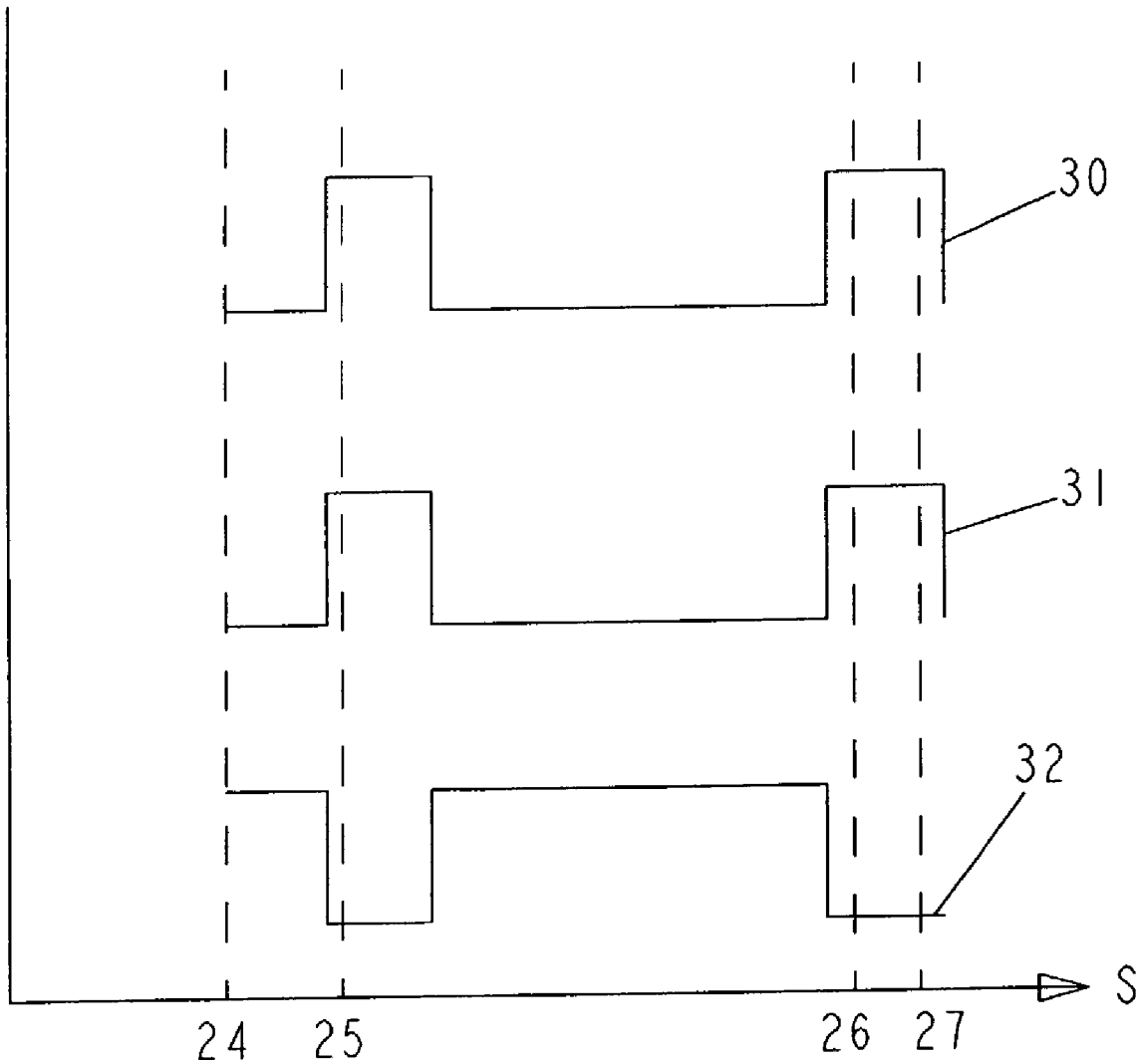
FIG. 9 shows a path diagram related to FIGS. 5 to 8.

This is shown in FIG. 9. The diagram shows the thrusting force 30, the generated thrusting torque 31, and the thrusting speed 32 of the plunger 7 in dependence on its position s for the procedure shown in FIGS. 5 to 8. The pitch of the transport spiral 7 is proportional to the thrusting speed 32.

One notices that the thrusting force 30 is already increased shortly before foil penetration 25 and working position 26 and, in consequence thereof, the thrusting speed 32 is reduced, wherein the increase or decrease is maintained along a certain path for properly satisfying the technical requirements for penetration through the foil, for positioning into the working position 26, and during expulsion 27, respectively.

Figure 10:
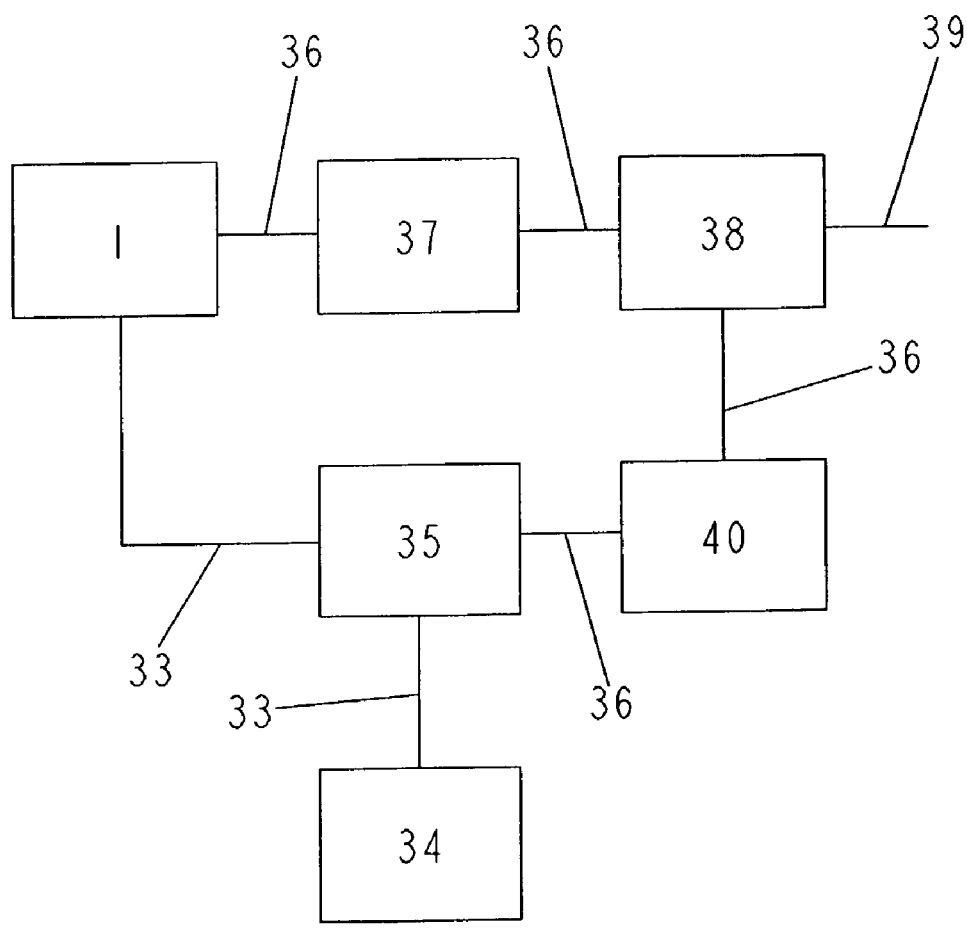
FIG. 10 shows a block diagram of a device in accordance with the invention having electronic regulation.

The block diagram of FIG. 10 illustrates how a position dependent plunger thrusting force can be effected using purely electronic means. Towards this end, the energy flow 33 from the battery 34 to a drive motor 1 is controlled. In order to facilitate high discharge of the battery, an amplifier 35 is utilized, which, when used together with a low impedance motor, can have a current limitation or, with pulse modulated operation, can have an output having current limitation. Control 36 is effected by means of a tachometer 37, a regulator 38 having set-point value input 39, and a pulse width modulated or linearly regulated output 40. This regulation is however not as efficient as a load dependent, mechanical transmission, since the drive motor 1 can not always be kept at an optimum working point.

LIST OF REFERENCE SYMBOLS 1 drive motor
2 transmission
3 drive wheel
4 carrier pin
5 transport spiral
6 rotation bearing
7 plunger
8 arrow
9 carrier member
10 receptacle bushing
11 carrier pin
12 carrier guide
13 bushing
14 blade
15 push-through opening
16 guide pin
17 positioning disc
18 sliding contact
19 receiving device
20 guide funnel
21 storage container
22 test element
23 measuring device
24 base position
25 foil penetration
26 working position
27 expulsion
28 insertion opening
29 removal opening
30 thrusting force
31 thrusting torque
32 thrusting speed
33 energy flow
34 battery
35 amplifier
36 controller
37 tachometer
38 regulator
39 set-point value
40 output
41 apertured plate
42 chamber
s position
50 analysis apparatus
52 power lines.

The invention claimed is:

1. A device for removing a consumable analytic product from a storage container, the device comprising
a drive wheel,
a control element being coupled to and formed for rotation with the drive wheel,
a carrier member in engagement with and formed for axial movement along the control element, and
a plunger situated within the control element and being formed for axial movement through the control element and engagement with the storage container, the magnitude of the thrusting force of the plunger relative to the storage container being dependent upon the position of the carrier member along the control element.

2. The device of claim 1 wherein the drive wheel is adapted to be electronically regulated to control the thrusting motion of the plunger.

3. The device of claim 1 further comprising a drive motor in communication with the drive wheel.

4. The device of claim 3 wherein the drive motor is formed to operate with substantially constant drive power.

5. The device of claim 3 wherein the drive motor is formed to operate with a substantially constant rate of revolution.

6. The device of claim 1 wherein the control element includes a transport spiral that is driven by the drive wheel for rotation about its longitudinal axis.

7. The device of claim 6 wherein the longitudinal axis of the spiral extends in the direction of thrusting motion of the plunger.

8. The device of claim 6 wherein the pitch of the transport spiral is constant.

9. The device of claim 6 wherein the pitch of the transport spiral changes along its helically shaped windings in correspondence to a desired thrusting force-position dependence for the plunger.

10. The device of claim 1 wherein the control element comprises a cylindrical drum controller having a groove in its outer surface and the carrier member comprises a tendon block engaging into the groove.

11. The device of claim 1 wherein the control element comprises a cylindrical helically wound transport spiral and the carrier element is configured as a carrier pin engaging into the windings of the transport spiral.

12. A device for removing a consumable analytic product from a storage container, the device comprising a drive wheel, a transport spiral formed for rotation with the drive wheel, a carrier member in engagement with and formed for axial movement along the transport spiral, and a plunger extending through the transport spiral and formed engagement with the storage container, the magnitude of the thrusting force of the plunger relative to the storage container being dependent upon the position of the carrier member along the transport spiral.

13. The device of claim 12 wherein the drive wheel is adapted to be electronically regulated to control the thrusting motion of the plunger.

14. The device of claim 12 further comprising a drive motor in communication with the drive wheel.

15. The device of claim 14 wherein the drive motor is formed to operate with substantially constant drive power.

16. The device of claim 14 wherein the drive motor is formed to operate with a substantially constant rate of revolution.

17. The device of claim 12 wherein the pitch of the transport spiral is constant.

18. The device of claim 12 wherein the pitch of the transport spiral changes along its helically shaped windings in correspondence to a desired thrusting force-position dependence for the plunger.

19. A device for removing a consumable analytic product from a storage container, the device comprising a drive wheel, a control element coupled to and formed for rotation with the drive wheel, the control element including a transport spiral, a carrier member in engagement with and formed for axial movement along the transport spiral, and a plunger extending through the transport spiral and drive wheel, the plunger being formed engagement with the storage container, the magnitude of the thrusting force of the plunger relative to the storage container being dependent upon the position of the carrier member along the transport spiral.

20. The device of claim 19 wherein the drive wheel is adapted to be electronically regulated to control the thrusting motion of the plunger.

21. The device of claim 19 further comprising a drive motor in communication with the drive wheel and formed to operate with substantially constant drive power.

22. The device of claim 19 further comprising a drive motor in communication with the drive wheel and formed to operate with a substantially constant rate of revolution.

23. The device of claim 19 wherein the pitch of the transport spiral is constant.

24. The device of claim 19 wherein the pitch of the transport spiral changes along its helically shaped windings in correspondence to a desired thrusting force-position dependence for the plunger.

* * * * *